United States Patent [19]

Hirano et al.

[11] Patent Number: 5,413,762
[45] Date of Patent: May 9, 1995

[54] DEVICE FOR THE PURIFICATION OF SYNTHETIC OLIGONUCLEOTIDES

[75] Inventors: Hideyasu Hirano, 20-111, Aobadaiminami 2-chome, Wakamatsu-ku, Kitakyushu-shi, Fukuoka-ken, Japan; Takayuki Emura, Fukuoka, Japan

[73] Assignees: Hideyasu Hirano; Astec Co., Ltd., both of Fukuoka, Japan

[21] Appl. No.: 159,073

[22] Filed: Nov. 29, 1993

[30] Foreign Application Priority Data

Dec. 4, 1992 [JP] Japan .................. 4-325624

[51] Int. Cl.⁶ .................. G01N 30/02; G01N 30/88
[52] U.S. Cl. .................. 422/70; 436/94; 210/656; 210/659; 935/1; 935/86; 935/88
[58] Field of Search .................. 436/94; 422/70; 210/656, 659; 435/270, 91, 287; 935/1, 86, 88

[56] References Cited

U.S. PATENT DOCUMENTS 4,948,882  8/1990  Ruth .................. 536/27
5,049,656  9/1991  Lewis et al. .................. 530/334

FOREIGN PATENT DOCUMENTS 9209615  6/1992  WIPO .

OTHER PUBLICATIONS

Gauer, R. K. "High-performance liquid chromatography of synthetic oligonucleotides." J. of Chromatography, 549 (1991) 207-215.
Seliger, H. et al. "Polymer Support Synthesis." J. of Chromatography, 397, (1987) 141-51.

*Primary Examiner*—David A. Redding
*Attorney, Agent, or Firm*—Jordan and Hamburg

[57] ABSTRACT

A device for the purification of synthetic oligonucleotides, characterized by comprising means for switching between purification with an affinity column which recognizes trityl groups, in cases where trityl groups are bonded, and purification with a disposable stepwise reverse phase chromatography column in cases where no trityl groups are bonded. The device makes it possible for any person to easily perform high-degree purification, simply by setting the synthesized oligonucleotides. Furthermore, it accomplishes both a method using an affinity column cartridge and a method for purification by HPLC.

9 Claims, 1 Drawing Sheet

DEVICE FOR THE PURIFICATION OF SYNTHETIC OLIGONUCLEOTIDES

BACKGROUND OF THE INVENTION

1. Field of the Invention

The present invention relates to an automated device for the purification of synthetic oligonucleotides.

2. Description of the Prior Art

In the fields of biotechnology and molecular biology, synthetic oligonucleotides are used as primers for the amplification of genes by PCR (POLYMERASE CHAIN REACTION, trademark of Cetus Co.), as primers for the amplification of RNA by PCR, for the preparation of mutant cDNA which is necessary for research on DNA-binding proteins, and for research for the preparation of proteins with mutated primary structures.

Oligonucleotides used for these purposes provide greater efficiency and a higher success rate when used in a highly purified form.

The present device may be used not only for the purposes of research, but also for examinations in hospitals and for criminal investigations by police.

In the past, such synthetic oligonucleotides have been purified manually, requiring significant time and labor, and thus creating the desire to develop a purification device.

In the past, purification has been carried out mainly by the following three methods.

1) Purification by repeatedly passing a reagent through an affinity column cartridge by use of a syringe.
2) Purification by high performance liquid chromatography (HPLC).
3) Purification using polyacrylamide gel.

SUMMARY OF THE INVENTION

The subject matter of the present invention concerns the provision of a device by which high-degree purification of synthetic oligonucleotides may easily be carried out by any person, simply by setting the synthesized oligonucleotides. It also concerns a single device equipped with means for accomplishing purification by a method using an affinity column cartridge and a method for purification by HPLC.

DETAILED DESCRIPTION OF THE INVENTION

Figure 1:
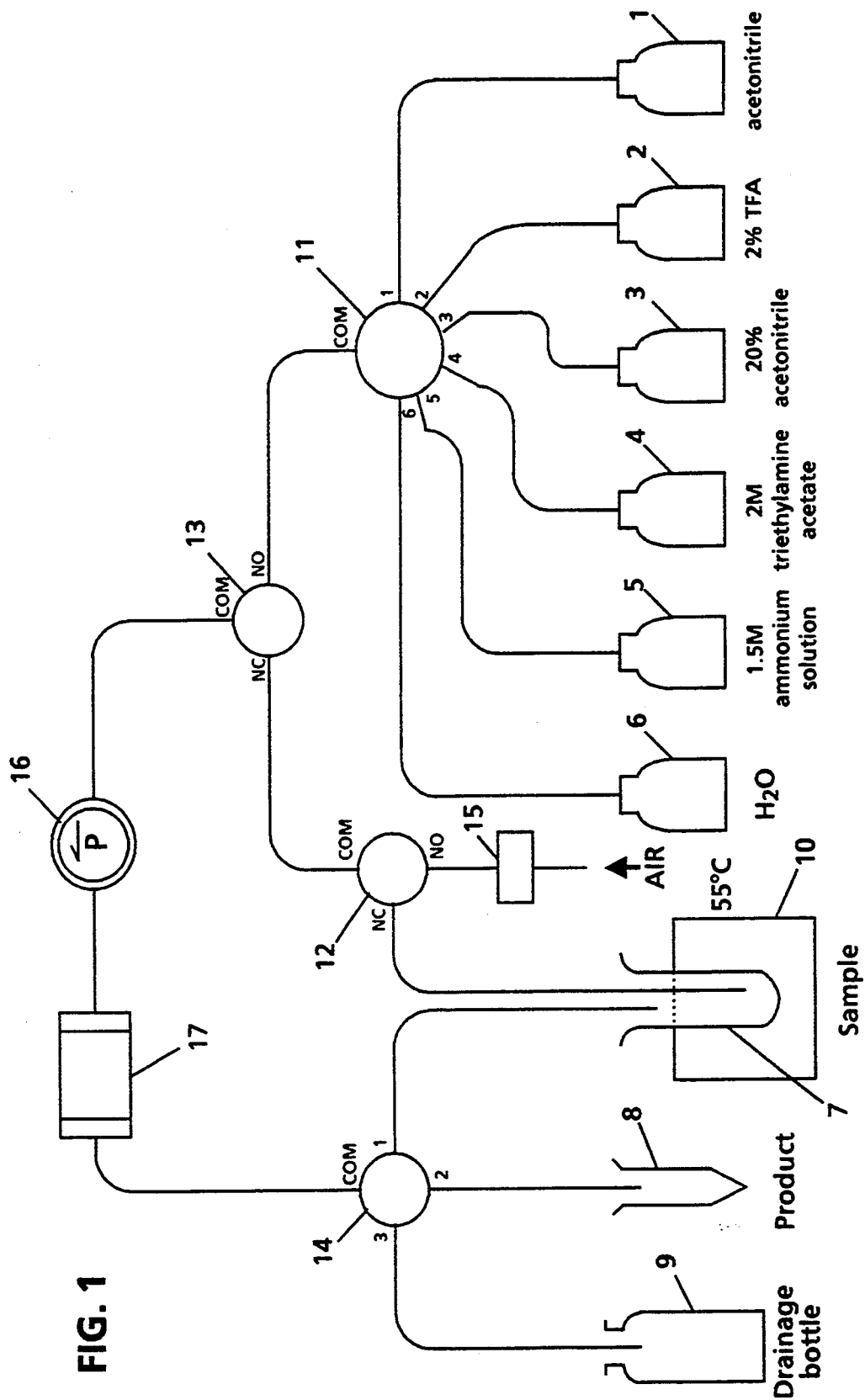
FIG. 1 is a constructional diagram showing an example according to the present invention.

In order to accomplish the above-mentioned object, the present invention provides a single device for the purification of both synthetic oligonucleotides with trityl groups and those without trityl groups.

a) Synthesized oligonucleotides with trityl groups
Purification is carried out using an affinity column cartridge.

b) Synthesized oligonucleotides without trityl groups
Purification is carried out by prefilling a disposable HPLC column with a filler exclusively used for synthetic nucleic acids, and by stepwise elution.

The method according to the present invention is carried out by the following steps.

I. Using an affinity column (for example, OPC (trademark) of Applied Biosystems, Inc.) cartridge
1. First, the column is pretreated with acetonitrile and 2M triethylamine acetate.
2. Next, a ⅓ equivolume of purified water is added to the synthesized oligonucleotides with trityl groups, and the mixture is passed through a column 3 times for binding to the filler.
3. Washing is effected with a 1.5M ammonium solution, and then with purified water.
4. The trityl groups bonded to the oligonucleotides are removed in 2% trifluoroacetic acid.
5. Washing is effected alternately with purified water, a 1.5M ammonium solution and purified water.
6. Elution is performed with 20% acetonitrile.

II. Using a disposable reverse phase column
1. First, the column is pretreated with acetonitrile and purified water.
2. Next, the oligonucleotides from which the trityl groups and protecting groups have been removed are placed in the column and washed with purified water, and then subjected to stepwise chromatography.
3. Elution is performed with 0–60% acetonitrile.

EXAMPLES

A more detailed description of the present invention will now be provided with reference to the Example.

Referring now to FIG. 1, reagent containers 1–6 are each filled with a reagent solution. According to the preferred embodiment, reagent containers 1–6 contain acetonitrile, 2% TFA (trifluoroacetic acid), 20% acetonitrile, 2M triethylamine acetate, 1.5M ammonium solution and purified water respectively. A sample container 7 is filled with a synthetic oligonucleotide which is to be purified, and is maintained at a controlled temperature of 55° C. by a heat block 10. A product container 8 collects the product following purification. A drainage bottle 9 collects any unused reagent passing through the system.

A first electromagnetic valve 11 having six input ports, each corresponding to a line communicating with an associated one of reagent containers 1–6, operates to output any one of the six input ports which is selected. The output of first electromagnetic valve 11 is sent to a second electromagnetic valve 13 having three ports. One of the remaining two ports of second electromagnetic valve 13 connects to a metering pump 16, which directs a measured amount of solution passing from second electromagnetic valve 13 into a column 17. The other remaining port of second electromagnetic valve 13 is connected with a third electromagnetic valve 12, also having three ports. Second electromagnetic valve 13 has a configuration which allows flow between any combination of two of the three ports, The two remaining ports of third electromagnetic valve 12 are respectively connected to sample container 7 and an air source filtered through an air filter 15. The configuration of third electromagnetic valve 12 restricts flow to between any combination of two of the three ports.

The type of purification column used for column 17 depends upon the nature of the synthetic oligonucleotide which is to be purified. Where the synthetic oligonucleotides contain bonded trityl groups, column 17 is an affinity column cartridge effective for such purification. However, where no trityl groups are bonded to the synthetic oligonucleotides, column 17 is an HPLC column with a filter used for nucleic acids, such as, for example, a disposable reverse phase column.

The operation of the device according to the present invention will be better understood with reference to the following examples I and II, describing the steps performed during the purification of a synthetic oligonucleotide containing bonded trityl groups, and one in which trityl groups are absent, respectively. Operation of electromagnetic valves 11, 12, 13, 14 in conjunction with metering pump 16, permits precise and efficient performance of the steps outlined below.

An explanation will now be provided regarding the method for the purification of synthetic oligonucleotides using the present device.

I. Using an OPC (trademark) cartridge as the affinity column

1. The sample in the sample container 7 is cultured at 55° C. for 12 hours.
2. Five milliliters of the acetonitrile in the container 1 are passed through the column 17 for pretreatment of the column 17.
3. Five milliliters of the 2M triethylamine acetate in the container 4 are passed through the column 17 for pretreatment of the column 17.
4. One milliliter of the purified water in the container 6 is added to the sample in the sample container 7.
5. The sample is passed through the column 17 three times, for binding thereof to the filler.
6. Fifteen milliliters of the 1.5M ammonium solution in the container 5 are passed through the column 17 for washing.
7. Ten milliliters of the purified water in the container 6 are passed through the column 17 for washing.
8. One milliliter of the trifluoroacetic acid in the container 2 is passed through the column 17 and, after 5 minutes, 4 ml thereof is passed through the column 17, for removal of the trityl groups.
9. Ten milliliters of the purified water in the container 6 are passed through the column 17 for washing.
10. Five milliliters of the 1.5M ammonium solution in the container 5 are passed through the column 17 for washing.
11. Ten milliliters of the purified water in the container 6 is passed through the column 17 for washing.
12. One milliliter of the 20% acetonitrile in the container 3 is passed through the column 17 for elution of the sample, and the eluate is collected in the product container 8 at the product.

II. Using a disposable reverse phase column as the affinity column.

1. The sample in the sample container 7 is cultured at 55° C. for 12 hours.
2. Ten milliliters of the acetonitrile the container 1 are passed through the column 17 for pretreatment of the column 17.
3. Ten milliliters of the purified water the container 6 are passed through the column 17 for pretreatment.
4. Four milliliters of the sample are passed through the column 17 and adsorbed in the column 17.
5. Ten milliliters of the purified water in the container 6 are passed through the column 17 for washing.
6. Stepwise chromatography is performed.
7. The 0–60% acetonitrile in the container 3 is passed through the column 17 for elution of the sample, and the eluate is collected in the product container 8 as the product.

As mentioned above, according to the present invention, synthetic oligonucleotides may be purified to a high degree easily by any person, simply by setting the synthesized oligonucleotides. Furthermore, a single device may accomplish both a method using an affinity column cartridge and a method for purification by HPLC.

We claim:

1. A device for the purification of a synthetic oligonucleotide, comprising:
    a plurality of reagent containers for holding reagent solutions therein;
    a sample container for holding said synthetic oligonucleotide therein;
    a column including an inlet and an outlet, said column further including means for purifying said synthetic oligonucleotide passed therethrough;
    a product container for holding therein a product obtained by purification of said synthetic oligonucleotide;
    means for selectively delivering a one solution into an inlet of said column for passage therethrough, said one solution selected from the group consisting of said reagent solutions and said synthetic oligonucleotide; and
    means for directing a discharging flow of said selected one solution passed through said column to one of said sample container, said product container and a drain.

2. The device according to claim 1, wherein:
    said synthetic oligonucleotide includes bonded trityl groups; and
    said column is an affinity column.

3. The device according to claim 1, wherein:
    said synthetic oligonucleotide is free from bonded trityl groups; and
    said column is a high performance liquid chromatography column.

4. A device for the purification of a synthetic oligonucleotide, comprising:
    a plurality of reagent containers, each for holding a reagent solution therein;
    a sample container for holding said synthetic oligonucleotide therein;
    a column including an inlet and an outlet, said column further including means for purifying said synthetic oligonucleotide passed therethrough;
    a product container for holding therein a product obtained by purification of said synthetic oligonucleotide;
    a first valve having a plurality of inlet ports and an outlet port, each of said plurality of inlet ports communicating with a corresponding one of said plurality of reagent containers, said first valve including means for selectively permitting flow from a selected one of said plurality of input ports, through said valve, to said outlet port;
    a second valve including at least three second valve ports, said second valve including means for permitting flow through said second valve between any selected combination of two of said at least three second valve ports, a first of said at least three second valve ports communicating with said outlet port of said first valve, a second of said at least three second valve ports communicating with said inlet of said column, a third of said at least three second valve ports communicating with said sample container;

means for pumping a selected solution to said column, said selected solution including one from the group consisting of said synthetic oligonucleotide and each said reagent solution; and a discharge valve including means for directing a discharging flow of said selected one solution passed through said column to one of said sample container, said product container and a drain.

5. The device according to claim 4, wherein:

said synthetic oligonucleotide includes bonded trityl groups; and said column is an affinity column.

6. The device according to claim 4, wherein:

said synthetic oligonucleotide is free from bonded trityl groups; and said column is a high performance liquid chromatography column.

7. A device for the purification of a synthetic oligonucleotide, comprising:

a plurality of reagent containers, each for holding a reagent solution therein;

a sample container for holding said synthetic oligonucleotide therein;

a column including an inlet and an outlet, said column further including means for purifying said synthetic oligonucleotide passed therethrough;

a product container for holding therein a product obtained by purification of said synthetic oligonucleotide;

a first valve having a plurality of inlet ports and an outlet port, each of said plurality of inlet ports communicating with a corresponding one of said plurality of reagent containers, said first valve including means for selectively permitting flow from a selected, one of said plurality of input ports, through said valve, to said outlet port;

a second valve including at least three second valve ports, said second valve including means for permitting flow through said second valve between any selected combination of two of said at least three second valve ports, a first of said at least three second valve ports communicating with said outlet port of said first valve, a second of said at least three second valve ports communicating with said inlet of said column;

a third valve including at least three third valve ports, said third valve including means for permitting flow through said third valve between any selected combination of two of said at least three third valve ports, a first of said at least three third valve ports communicating with a third of said at least three second valve ports, a second of said at least three third valve ports communicating with an air source, a third of said at least three third valve ports communicating with said sample container;

means for pumping a selected solution to said column, said selected solution including one from the group consisting of said synthetic oligonucleotide and each said reagent solution; and a discharge valve including means for directing a discharging flow of said selected one solution passed through said column to one of said sample container, said product container and a drain.

8. The device according to claim 7, wherein:

said synthetic oligonucleotide includes bonded trityl groups; and said column is an affinity column.

9. The device according to claim 8, wherein:

said synthetic oligonucleotide is free from bonded trityl groups; and said column is a high performance liquid chromatography column.

* * * * *